US008016818B2

(12) United States Patent
Ellis et al.

(10) Patent No.: US 8,016,818 B2
(45) Date of Patent: Sep. 13, 2011

(54) TACTILE AMPLIFICATION INSTRUMENT AND METHOD OF USE (75) Inventors: Randy E. Ellis, Kingston (CA); Vincent Hayward, Westmont (CA); Hsin-Yun Yao, Deux-Montagnes (CA)

(73) Assignees: McGill University, Montreal, Quebec (CA); Queen's University at Kingston, Kingston, Ontario (CA)

( * ) Notice: Subject to any disclaimer, the term of this patent is extended or adjusted under 35 U.S.C. 154(b) by 1360 days.

(21) Appl. No.: 11/526,237

(22) Filed: Sep. 25, 2006

(65) Prior Publication Data
US 2007/0135735 A1 Jun. 14, 2007

Related U.S. Application Data (60) Provisional application No. 60/719,564, filed on Sep. 23, 2005.

(51) Int. Cl.
*A61B 17/00* (2006.01)
(52) U.S. Cl. ............................................. 606/1; 600/587
(58) Field of Classification Search .................. None
See application file for complete search history.

(56) References Cited

U.S. PATENT DOCUMENTS

| | | | |
|---|---|---|---|
| 5,533,519 A | 7/1996 | Radke et al. | |
| 5,609,607 A | 3/1997 | Hechtenberg et al. | |
| 6,020,876 A * | 2/2000 | Rosenberg et al. | 345/157 |
| 6,096,004 A | 8/2000 | Meglan et al. | |
| 6,184,868 B1 | 2/2001 | Shahoian et al. | |
| 6,364,849 B1 | 4/2002 | Wilcox | |
| 6,432,112 B2 | 8/2002 | Brock et al. | |
| 6,589,287 B2 | 7/2003 | Lundborg | |
| 6,969,384 B2 | 11/2005 | de Juan, Jr. et al. | |
| 2001/0000663 A1 | 5/2001 | Shahoian et al. | |
| 2001/0025150 A1* | 9/2001 | de Juan et al. | 600/587 |
| 2002/0062177 A1 | 5/2002 | Hannaford et al. | |
| 2002/0112547 A1 | 8/2002 | Eltaib et al. | |
| 2002/0133175 A1 | 9/2002 | Carson | |
| 2002/0147455 A1 | 10/2002 | Carson | |
| 2003/0057973 A1 | 3/2003 | Nojima et al. | |
| 2003/0069591 A1 | 4/2003 | Carson et al. | |

(Continued)

FOREIGN PATENT DOCUMENTS

EP 0970663 1/2000

OTHER PUBLICATIONS

Yao, "Touch Magnifying Instrument Applied to Minimally Invasive Surgery" Sep. 14, 2004, McGill University.*

(Continued)

*Primary Examiner* — Sam Yao
*Assistant Examiner* — Lynsey Crandall
(74) *Attorney, Agent, or Firm* — Stephen J. Scribner; Angela Lyon (57) ABSTRACT The invention relates to a tool comprising a handle and a tip, which provides amplified tactile feedback to a user regarding the material with which the tip of the tool is in contact. In one embodiment, tactile feedback is provided to the user via the handle of the tool, in the form of movements which correspond at least partially to those experienced by the tip of the tool as it interacts with the material. The tool optionally provides audio and/or visual feedback regarding the material. In a preferred embodiment, the tool is a surgical instrument.

24 Claims, 4 Drawing Sheets

U.S. PATENT DOCUMENTS

2004/0019447 A1     1/2004    Shachar
2004/0106916 A1     6/2004    Quaid et al.

OTHER PUBLICATIONS

Yao, Hsin-Yun, et al., "A tactile magnification instrument for minimally invasive surgery." MICCAI, LNCS vol. 3217, pp. 89-96 (Sep. 23, 2004).

Yao, Hsin-Yun, "Touch magnifying instrument applied to minimally invasive surgery." Thesis, McGill University (Sep. 2004).

Yao, Hsin-Yun, et al., "A tactile enhancement instrument for minimally invasive surgery." Computer Aided Surgery, 10(4): 233-239 (Jul. 2005).

Yao, Hsin-Yun, et al., "A tactile magnification Instrument for minimally invasive surgery." 15th Annual Canadian Conference on Intelligent Systems, Quebec City, Canada (Jun. 5-7, 2005).

Basdogan, C., et al.,"Haptics in minimally invasive surgical simulation and training." IEEE Computer Graphics and Applications, 24(2): 56-64 (2004).

Howe, R.D., et al., "Remote palpation technology." IEEE Engineering in Medicine and Biology 14(3): 318-323 (1995).

"Tools for minimally invasive surgery" http://www.piaggio.ccii.unipi.it/robotics/robresearch/misurgery.html.

\* cited by examiner

TACTILE AMPLIFICATION INSTRUMENT AND METHOD OF USE

RELATED APPLICATIONS

This application claims the benefit of the filing date of U.S. Provisional Patent Application No. 60/719,564, filed 23 Sep. 2005, the contents of which are incorporated herein by reference in their entirety.

FIELD OF THE INVENTION

The invention is in the field of surgical tools. In particular, the invention relates to tools for minimally-invasive surgery.

BACKGROUND OF THE INVENTION

Minimally-invasive surgery offers benefits to patients through the use of small sized incisions which cause less pain, less trauma, and shorter healing periods than larger incisions. However, minimally-invasive surgery requires that the surgeon cope with little or no direct tactile information and reduced visual information of the tissue at the surgical site. It has been demonstrated that even partial restoration of the sense of touch improves performance in teleoperation and virtual environments (Kontarinis et al., Rosen et al., Okamura et al., Pai et al.). Systems designed to improve human performance in surgical applications often feature visual feedback (Dario et al.). For example, during arthroscopic surgery wherein a fibre optic scope is inserted into a joint to allow visualization of internal structures, a surgeon views the anatomy via one incision and inserts a surgical instrument through another small incision.

Surgery may be required in regions that cannot be seen arthroscopically; in such cases, a surgeon must rely completely on tactile feedback obtained through the hand via a surgical instrument. In such cases, arthroscopic instruments which improve tactile feedback may be employed. One such instrument commonly used has a metal tip on the end of a handle. Many different shapes of tips are available, but the arthroscopic hook, with a tip bent to a 90° angle, is particularly useful. With such an instrument, a surgeon is able to probe tissues to find damage and anomalies and to perform surgical procedures.

There is, however, a need for a surgical instrument that improves tactile feedback to the user.

SUMMARY OF THE INVENTION

According to one aspect of the invention there is provided a tool for obtaining tactile information about a material, comprising a tip for contacting the material; a handle attached to the tip; a sensor in mechanical communication with the tip, the sensor receiving information about the interaction of the tip with the material, such information being along a first axis, and producing a signal from the first axis information; an amplifier for receiving and amplifying the signal to produce an amplified signal; and an actuator disposed in the handle for receiving the amplified signal and producing an output motion along a second axis different from the first axis.

In one embodiment the second axis may be parallel to a longitudinal axis of the tool and the second axis orthogonal. In another embodiment, the first and second axes may be both orthogonal to the longitudinal axis of the tool.

In another embodiment, the invention provides a tool for obtaining tactile information about a material, comprising: a tip for contacting the material; a handle attached to the tip; a sensor in mechanical communication with the tip, the sensor receiving information about the material from the tip, such information being along a first axis and a second axis different from the first axis, and producing a signal from the first axis and second axis information; an amplifier for receiving and amplifying the signal to produce an amplified signal; and an actuator disposed in the handle for receiving the amplified signal and producing an output motion along a third axis different from the first axis and the second axis.

In one embodiment, the third axis may be parallel to a longitudinal axis of the tool. In another embodiment, the first, second, and third axes may be orthogonal.

According to another aspect of the invention there is provided a system for remotely obtaining tactile information about a material, comprising: a first tool comprising: a tip for contacting the material; a handle attached to the tip; a sensor in mechanical communication with the tip, the sensor receiving information about the material from the tip; an amplifier for receiving and amplifying the signal to produce an amplified signal; and a second tool comprising: a handle; and an actuator disposed in the handle for receiving the amplified signal and producing an output motion in the handle.

The tool may further comprise an audio transducer for receiving the amplified signal and producing an audio output, and the sensor may be an accelerometer. In another embodiment of the tool, the output motion may be a vibration.

In one embodiment, the actuator comprises: a magnet resiliently suspended inside the handle; and a wire coil proximal to the magnet, the coil receiving the amplified signal; wherein the amplified signal induces motion of the magnet relative to the coil and the handle.

In a preferred embodiment, the tool is a surgical instrument.

According to another aspect of the invention there is provided a method for obtaining tactile information about a material, comprising: providing a tool having a handle and a tip for contacting the material; contacting the material with the tip; sensing tactile information about the material from the tip and converting the information into an electrical signal, the information being along a first axis; amplifying the signal to produce an amplified signal; and using the amplified signal to produce motion in the handle, the motion related to the sensed tactile information from the tip; wherein the motion is along a second axis different from the first axis.

According to another aspect of the invention there is provided a method for remotely obtaining tactile information about a material, comprising: providing a first tool having a handle and a tip for contacting the material; contacting the material with the tip; sensing tactile information about the material from the tip and converting the information into an electrical signal; amplifying the signal to produce an amplified signal; providing a second tool; and using the amplified signal to produce motion in the second tool.

In one embodiment, the tactile information may be along a first axis and the motion being along a second axis different from the first axis.

According to an embodiment of the method of the invention, the tool is a surgical instrument and the material is human or non-human tissue. The method may be a surgical procedure. The procedure may involve dissection or separation of tissue. The procedure may involve piercing tissue.

According to another aspect of the invention there is provided a kit comprising a tool as described above and a sheet of instructions for use thereof.

Another aspect of the invention relates to a tool for obtaining tactile information about a material, comprising: a tip for interacting with the material to produce a vibration; a handle attached to the tip; a sensor in mechanical communication with the tip, the sensor receiving vibration from the tip and producing an electrical signal from the vibration; an amplifier for receiving and amplifying the electrical signal to produce an amplified signal; and an actuator disposed in the handle for receiving the amplified signal and producing related output motion; wherein the output motion and the vibration are decoupled.

The vibration of the tip may be along a first axis and the output motion may be along a second axis different from the first axis. The vibration of the tip may be along a first axis and a second axis different from the first axis, and the output motion may be along a third axis different from the first axis and the second axis. In other embodiments, the first and second axes may be orthogonal, or the first, second, and third axes may be orthogonal.

The tool may further comprise an audio transducer for receiving the amplified signal and producing an audio output. The output motion may be along an axis parallel to a longitudinal axis of the tool.

In one embodiment, the sensor may be an accelerometer.

The output motion may be a vibration.

The actuator may comprise: a magnet resiliently suspended inside the handle; and a wire coil proximal to the magnet, the coil receiving the amplified signal; wherein the amplified signal induces motion of the magnet relative to the coil and the handle.

In one embodiment, the tool is a surgical instrument.

Another aspect of the invention relates to a system for remotely obtaining tactile information about a material, comprising: a primary tool as described above; and at least one secondary tool, each secondary tool comprising: a handle; and an actuator disposed in the handle for receiving the amplified signal from the primary tool and producing an output motion in the handle.

The vibration of the tip may be along a first axis and the output motion may be along a second axis different from the first axis. The vibration of the tip may be along a first axis and a second axis different from the first axis, and the output motion may be along a third axis different from the first axis and the second axis.

In one embodiment, the sensor may be an accelerometer.

Another aspect of the invention relates to a method for obtaining tactile information about a material, comprising: providing a tool having a handle and a tip for interacting with the material to produce a vibration; contacting the material with the tip; sensing vibration of the tip and converting the vibration into an electrical signal; amplifying the signal to produce an amplified signal; and using the amplified signal to produce motion in the handle, the motion related to the vibration of the tip; wherein the output motion and the vibration are decoupled.

Another aspect of the invention relates to a method for remotely obtaining tactile information about a material, comprising: providing a primary tool as described above; providing at least one secondary tool, each secondary tool comprising: a handle; and an actuator disposed in the handle for receiving the amplified signal and producing an output motion in the handle; and using the amplified signal from the primary tool to produce motion in each secondary tool.

Such aspect may comprise sensing vibration along a first axis, and producing the motion along a second axis different from the first axis. The method may relate to a surgical procedure.

BRIEF DESCRIPTION OF THE DRAWINGS

Embodiments of the invention will now be described, by way of example, with reference to the accompanying drawings, wherein.

DETAILED DESCRIPTION OF THE INVENTION

According to one aspect, the invention relates to a tool for obtaining tactile information about a material. The tool may be a probe having a handle and a tip for interacting with the material to produce information about the material, which information may be in the form of minute vibrations generated in the tip as it interacts with the material. A sensor in mechanical communication with the tip receives the information from the tip, producing an electrical signal. The electrical signal may then be used to provide the information from the tip to the user, in the form of tactile, audio, and/or visual feedback. For example, tactile feedback may be provided mechanically by generating an output motion (e.g., vibration) in the handle which relates to the vibration of the tip. Such tactile feedback is mechanically decoupled from the vibrations of the probe tip.

According to one embodiment, the invention relates to a tool comprising a handle and a tip, which provides amplified tactile feedback to a user regarding the nature of the material with which the tip of the tool is in contact. Tactile feedback is provided to the user via the handle of the tool, in the form of movements or vibrations which correspond at least partially to those experienced by the tip of the tool as it is moved over and/or through the material. Accelerations experienced by the tip of the tool may be used selectively to determine the tactile feedback provided. In one embodiment, the tool is a surgical instrument and the material with which the tip of the tool is in contact is biological (e.g., human or non-human) tissue, such as, for example, skin, muscle, connective tissue, cartilage, bone, or the like. The tool of the invention may additionally provide auditory and/or visual feedback to the user regarding the nature of the material with which the tip of the tool is in contact. For example, the tool may provide visual feedback in the form of information presented on a video display, to inform the user of the nature of the material contacted by the tool tip. As used herein, the phrase "nature of the material" refers to surface features, density, thickness, condition (damaged, intact, abnormal, etc.), and/or any other characteristic of the material that can be obtained tactually.

According to this aspect of the invention, the tip of the tool may be of any shape suitable for the intended use, such as straight, curved, or bent. In surgical applications, the tip may have, for example, a 90 degree bend, such as that shown in FIGS. 1A and 1B. The tip may be made of metallic (e.g., stainless steel) or non-metallic (e.g., plastic, Nylon®) materials, and have appropriate rigidity for the type of material being investigated. For example, soft materials may require a more flexible tip than hard materials. In any case, the tip of the tool is in mechanical communication with a transducer (also referred to herein as a sensor) that transforms mechanical stimuli received by the tip as it passes over and/or through material, to an electrical signal. The stimuli, which produce vibrations in the tip, result from physical interactions between the tip of the tool and the material, and include, for example, stress, strain, force, acceleration. Examples of suitable transducers include, but are not limited to, force sensors and accelerometers. Force sensors may be, for example, of piezo-electric, piezo-ceramic, piezo-polymer, or piezo-resistive materials, or optical fiber flexion sensors. Accelerometers may be realized with, for example, micro-electro-mechanical systems (MEMS) technology.

However, the inventors have found that small changes in the nature of the material being probed can more accurately and more rapidly be detected using accelerometers rather than force sensors. Without wishing to be bound by theory, it is suggested that the difference is related to the fact that force sensors sense force indirectly (e.g., by sensing strain), and produce a relatively steady-state output signal from which force may be deduced and quantified from knowledge of the mechanical behaviour of the sensor material. Accelerometers, on the other hand, sense acceleration and are relatively insensitive to long term changes in movement or movement at constant velocity. Accelerometers therefore perform well as, for example, vibration sensors, where changes in vibration may be detected rapidly and qualitatively. Accelerometers are thus well suited to the invention, where vibrations of the probe tip change as, for example, the tip contacts a change in a material and/or different material types during use.

The electrical signal produced by a transducer as described above is usually of a small magnitude. Accordingly, the signal may be processed as required, which may include filtering and/or conditioning, and then amplified to a magnitude suitable for driving an output device. The output device may comprise an actuator, disposed in the handle of the tool, that converts the amplified electrical signal into a mechanical signal (e.g., a movement or vibration) which can be felt in the hand of the user of the tool, thereby providing tactile feedback to the user. The movements or vibrations produced by the actuator in the handle of the tool are provided to the user at a frequency and magnitude that are easily detectable by the user, even when the material being contacted is undetectable using a tool without amplified tactile feedback.

One embodiment of the actuator comprises a permanent magnet and at least one coil. For example, the actuator may comprise a cylindrical magnet resiliently suspended inside the handle which magnetically interferes with the coil. Upon activation of the coil (by passing an electric current through the coil), a mutual force develops between the magnet and the handle. For frequencies above resonant frequency of the handle, the handle accelerates over small displacements in phase that is opposite to the phase of the magnet. If the mass of the magnet is significant with respect to that of the handle, the actuator provides a heightened tactile sensation of the vibratory movements of the tip. Users perceive the amplified tactile signals as an enhanced sense of touch.

High amplification gains can be achieved because the actuator causes the handle to vibrate in a direction different from that of the acceleration detected at the tool tip (as discussed below). A preferred embodiment of the actuator comprises an open magnetic circuit structure comprising a magnet (e.g., a cylindrical rare earth magnet (NdFeB)) elastically suspended inside the handle, and two coils. The field lines escaping the magnet cross the loops of the two coils at right angles, thereby developing a Lorentz force between the magnet and the handle when current flows through the coils. The two coils encircle the handle proximal to the north pole of the magnet and to the south pole of the magnet. These coils may be located on the exterior of the handle, but in preferred embodiments the coils are on the interior of the handle or encased in the handle material to allow for ease of cleaning. In one embodiment the accelerometer detects acceleration of the tool tip in either or both of two axes, both of which are different from the longitudinal axis of the cylindrical magnet, the tool, and the tool handle.

It will be appreciated that as the tip of the tool is moved through a material, it will experience movement (e.g., vibration) in three dimensions. The inventors have recognized that under certain circumstances the actuator may produce a mechanical signal along an axis that is aligned with an axis of a stimulus, resulting in coupling of the feedback signal with the stimulus. Such coupling may have undesirable effects, such as destabilizing the tool and/or confounding the signal. The inventors have found that this potential problem can be avoided by decoupling the feedback signal in the handle from the tip of the tool. Such mechanical decoupling may be accomplished by orienting the actuator feedback signal along an axis different from the axis or axes of the stimulus or stimuli being tracked by the tool. For example, in a Cartesian coordinate system having three axes x, y, z, where only stimuli in the x axis are being detected, the actuator feedback signal may be oriented along either the y or z axes. Similarly, for example, where stimuli in the x and y axes are being detected, the actuator feedback signal is oriented along the z axis. However, whereas it is preferred that the axes of the stimuli being detected and the actuator feedback signal be orthogonally opposed, this is not required. Rather, it is only required that the axes of the stimuli and the axis of the actuator signal be different enough to provide decoupling. In this respect the tool of the invention is substantially different from devices such as that proposed in U.S. Pat. No. 6,969,384, issued Nov. 29, 2005 to de Juan, Jr. et al., where the problem of coupling between the signal from the tip of the device and mechanical feedback in the handle of the device is not addressed or solved.

Figure 1:
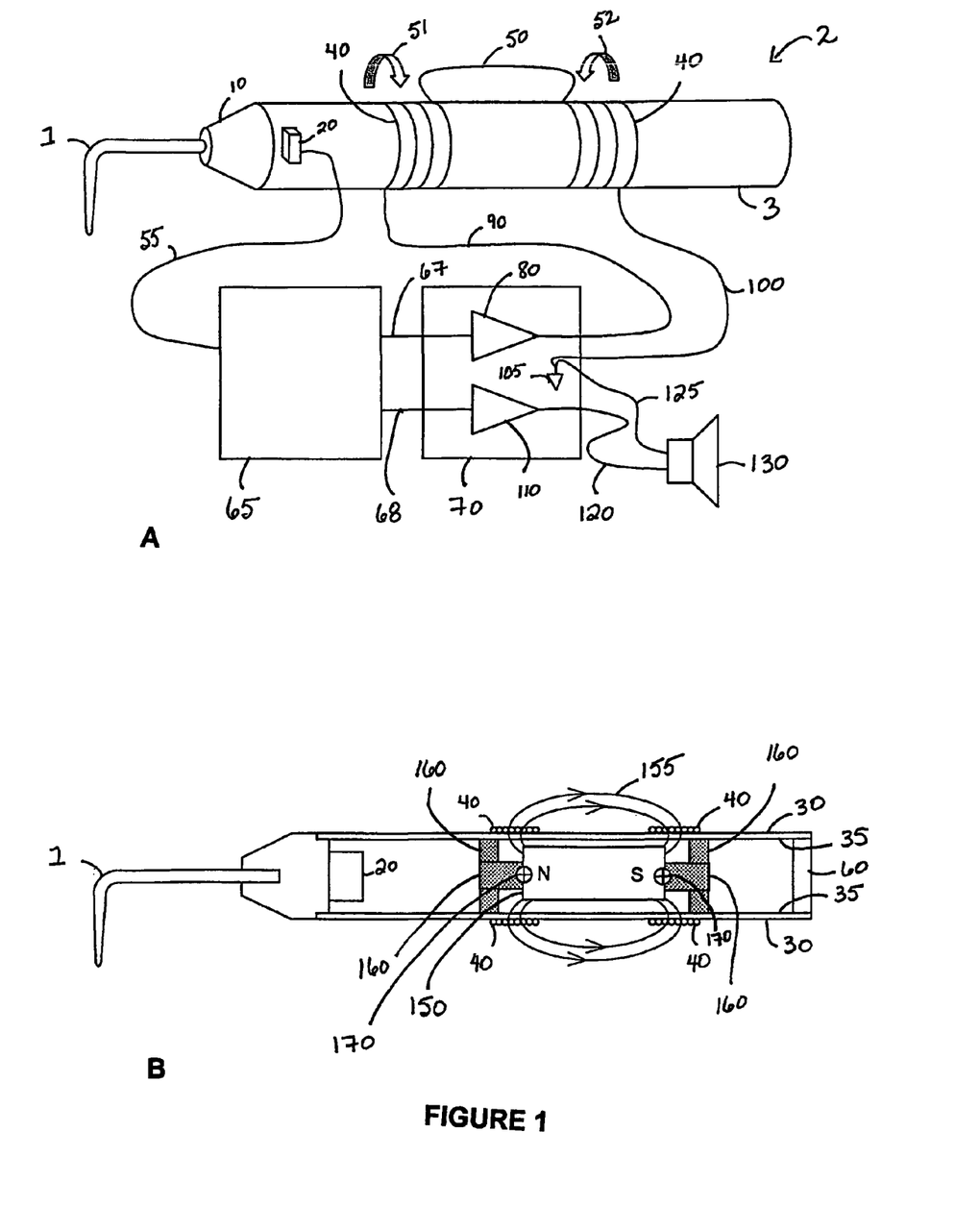
FIG. 1A is a schematic drawing of a tool of the invention.
FIG. 1B is a schematic drawing of a cross section the tool of FIG. 1A.

In accordance with this aspect of the invention, the transducer (e.g., accelerometer) may be oriented to measure acceleration of the tip of the tool in directions radial to a longitudinal axis of the handle, while the actuator is oriented so as to produce the feedback signal along the longitudinal axis of the handle. Such an embodiment is shown in FIGS. 1A and 1B. In another embodiment, the transducer senses stimuli along a first axis and along a second axis which is orthogonal to the first axis, and produces an electrical signal which is amplified and sent to an actuator located in the handle that receives the amplified signal and produces a mechanical feedback signal along a third axis orthogonal to the first and second axes. Providing the tactile feedback signal along a single different axis has the effect of dynamically decoupling the input from the output, greatly improving the stability margin of the tool.

In one embodiment, the tool is sealed water/air tight to allow for washing and sterilizing of the device. In another embodiment, the tip is removable so that worn-out or contaminated tips may be replaced with new and/or sterilized tips. In another embodiment, the tool is a low cost, disposable, single-use device. In a further embodiment, the tool is provided in a kit, which may be packaged in sterile form, optionally with replacement tips, some of which may be of various shape, size, and rigidity, and with an instruction sheet for use of the tool.

The tool facilitates tactile assessment of injuries such as, for example, torn tissue and damaged joints. The tool also facilitates tactile assessment of surface and subsurface structures, such as veins, arteries, lumens, etc., including abnormalities such as tumours and the like, in tissues such as ligaments and muscles, and in menisci, joints and cartilage. The tool may be used in such examinations to determine the extent and nature of tissue injuries. Such examinations may be performed, for example, on athletes and animals such as race horses. The tool also facilitates procedures such as dissecting and separating tissues, where tactile differences in multiple tissues in close proximity (e.g., layered) may be difficult to detect without amplified tactile feedback.

In another embodiment, the tip of the tool is a needle that allows tactile detection of penetration or piercing of the needle through a surface or subsurface structure or tissue, such as the piercing of the skin or other epithelial tissue, or organs such as the stomach, heart, bowel, or luminal structures such as a blood vessel, trachea, bronchi, intestine, brain ventricle, etc. In such embodiment the needle may be provided with a Leur Lock device.

Accelerometers useful for the invention may be 1-dimensional, 2-dimensional or 3-dimensional sensors. 3-dimensional sensors are preferred for embodiments of the invention which provide audio feedback. Several types of accelerometers are available commercially, for example, piezo-resistor, piezo-electric, silicon bridge, micro-machined silicon, and voice-coil. Preferred accelerometers are micro-machined silicon with the capability to sense both AC accelerations (typical of vibration) and DC accelerations (such as inertial force or gravity). In particular, it was found that the ADXL311 accelerometer from Analog Devices (Norwood, Mass., U.S.A.) was suitable. This low cost, low power, single and dual axis sensor can sense both dynamic acceleration (e.g., vibration) and static acceleration (e.g., gravity), and has built-in signal conditioning circuits that produce analog voltages proportional to acceleration.

A preferred embodiment of the tool of the invention is shown in FIGS. 1A and 1B. Referring to FIG. 1A, the tool has a handle 3 substantially defined by a wall 30, and a tip 1 for engaging a material to be examined. In the embodiment shown in the figures, the tip has a 90 degree bend. The tip is attached to the handle by, for example, having its shaft pressed (e.g., a friction fit) into a cap 10, which fits securely into the hollow handle. The handle has an end cap 60 at the end distal to the tip 1. The cap 10 and the end cap 60 preferably form a fluid-tight seal with the handle, to prevent liquid, moisture, etc., from entering the handle.

The tool has a sensor 20 (e.g., accelerometer) which is disposed in mechanical communication with the tip 1. The sensor is electrically connected to a signal processing unit 65 which may provide signal processing functions such as filtering, etc., and splits the signal into first and second signals. The first signal is sent to a first amplifier 80, which is electrically connected to a pair of coils 40 wrapped around the handle 3. The first amplifier 80 amplifies the first signal, which signal is then provided to the coils 40. The second signal from the processing unit 65 is provided to a second amplifier 110, which amplifies the second signal, which signal is then provided to an audio transducer 130 (e.g., a loudspeaker) which produces audio feedback. It will be appreciated of course that provision of audio feedback is optional and thus the splitter, second amplifier, and loudspeaker may be omitted if audio feedback is not desired.

In FIG. 1B, interior components of the tool are shown. Elastic elements 160 are attached to the interior surface 35 of the wall 30 of the handle. A cylindrical magnet 150 is secured at each end between the elastic elements such that the magnet is suspended inside the handle by the elastic elements. The coils 40 are located proximal to the poles of the magnet such that the magnetic field generated by the magnet intersects the coils substantially perpendicularly. The coils, elastic elements, and magnet form the actuator.

The coils 40 are electrically connected and configured to allow current to flow in opposite directions to one another (as indicated by the arrows 51 and 52 of FIG. 1A). The coils are located proximally to the poles of the magnet which are indicated in FIG. 1B as N (north) and S (south). The current of the amplified signal flowing in the coils intersects the magnetic field of the magnet and causes the magnet to move. This produces an output tactile signal which is perceived by a user who is holding the tool. As noted above, the output tactile signal is produced along one or more axes chosen appropriately for stabilizing the tool. In FIGS. 1A and 1B, the tactile signal is oriented along the longitudinal axis of the tool.

The signal processing circuitry 65, amplifier 80, and optionally amplifier 110 and loudspeaker 130, may be disposed remotely from the tool, in which case they may be electrically connected to the tool via wires, such as those (55, 90, 100) shown in FIG. 1A, or via a wireless connection. Alternatively, the signal processing circuitry 65, amplifier 80, and optionally amplifier 110 and loudspeaker 130, may be disposed inside the tool, resulting in a self-contained unit. Such an embodiment would additionally require a power supply, such as a battery, included within the tool.

A signal representing surface contact of the tip is sent from the sensor to a signal processing unit where the signal is amplified and optionally signal shaping and filtering may be performed, for example, with analog circuitry or a digital signal processor. A preferred signal-processor is the Blackfin 533 available from Analog Devices (Norwood, Mass., U.S.A.). A digital signal processor allows more flexibility in terms of filtering and signal shaping and enables recording, play-back, and storage of tactile signals. It is noted that in a simple configuration of the tool, the accelerometer voltage output can, with some amplification, be directly used as input to the actuator without signal processing.

Figure 2:
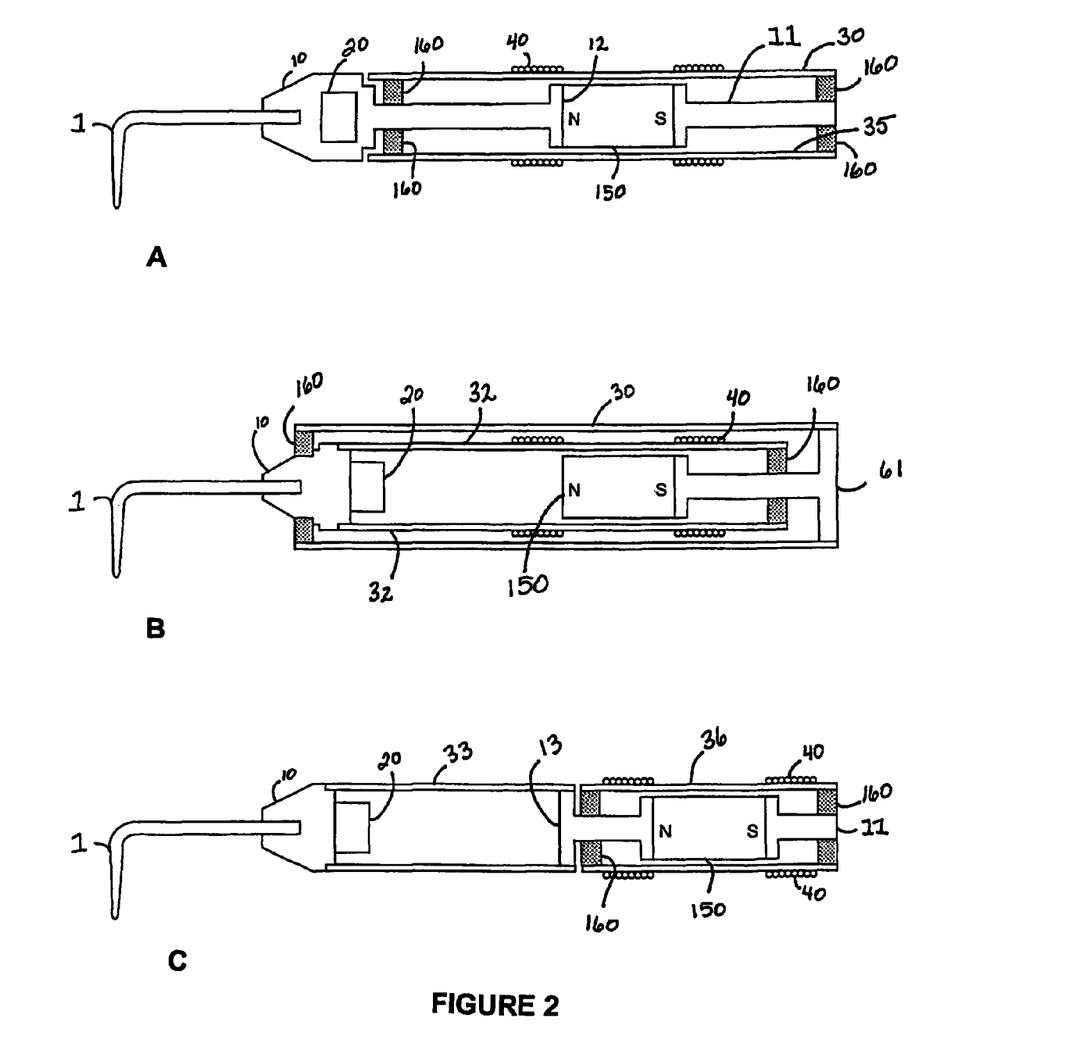
FIGS. 2A, 2B, and 2C are schematic drawings of cross-sections of further embodiments of the invention showing variations on the arrangement of the actuator.

FIGS. 2A, 2B, and 2C show further embodiments based on variations on how the actuator is configured. In the following description, the term "proximal" refers to an end of the tool closest to the tip, and the term "distal" refers to an end of the tool farthest from the tip. In the embodiment of FIG. 2A, the magnet 150 is secured by substantially rigid members 11, 12. Member 11 is connected to a distal end of tube 30 via an elastic element 160. Member 12 is rigidly connected to cap 10. The tube 30 is resiliently connected to the cap 10 and member 12 via an elastic element 160. In another embodiment, the magnet 150 is attached to one of the handle and the cap via a substantially rigid mechanical connection, and to the other of the handle and the cap via an elastic element 160, as shown in FIG. 2B. In particular, the embodiment of FIG. 2B includes an end cap 61 which connects the magnet to the distal end of the handle, and an inner tube 32 coaxial with the tube 30 of handle 3. The proximal end of the tube 32 is connected to the cap 10 via a substantially rigid mechanical connection, and the distal end of the tube 32 is connected to the end cap 61 via an elastic element 160. The outer tube 30 is connected at the distal end to the end cap 61 and at the proximal end to the cap 10 via an elastic element 160. In the embodiment of FIG. 2C, the handle comprises first and second tubular portions 33 and 36. One end of the magnet 150 is secured to the distal end of the second handle portion 36 in a manner similar to that of FIG. 2A, with a substantially rigid member 11 and an elastic element 160. The other end of the magnet 150 is connected to the distal end of the first handle portion 33 via a substantially rigid member 13. The proximal end of the second handle portion 36 is resiliently connected to member 13 via an elastic element 160.

As noted above, the sensor 20 is disposed such that it is in vibratory communication with any the tip 1, so as to receive force, acceleration, etc. experienced by the tip. Depending on the sensor employed, the sensor may provide a voltage signal or a current signal, the magnitude of the signal being related to the magnitude of the force or acceleration received by the tip.

In all embodiments, the sensor 20 may be disposed near the tip for greater sensitivity. This may be accomplished by directly packaging the microscopic accelerometer elements of a MEMS device inside a hollowed portion of the shaft terminating at the tip.

The handle may be of any size and shape suitable for hand-held use. For example, although the embodiments in the attached figures are cylindrical, other shapes may be more suitable for surgical or other (e.g., non-surgical) applications. Preferably the handle is rigid and light-weight. For example, the handle may be 5 mm in diameter and 180 mm in length, and made of carbon fiber tubing.

In another embodiment of the invention, a second sensor is located near the actuator and provides a feedback signal to the signal processing unit. This embodiment provides more information and allows for increased control of the tactile feedback provided by the tool. This feature may be useful in acquiring second opinions regarding diagnoses and/or for teaching.

In another embodiment of the invention, the signal from the sensor is amplified and sent to an auditory transducer (e.g., loudspeaker). As discussed in the Example and shown in Table 1, below, users that were provided auditory feedback from the sensor instead of amplified tactile information had an improved ability to detect small cuts in a surface.

Other embodiments of the invention use variable reluctance actuators, and a tubular soft-iron magnetic return. Acceleration of the handle was maximized by minimizing the mass of the shell, maximizing the mass of the moving part, and maximizing force. In one embodiment, 5 W of electrical power caused vibrations of sufficient magnitude for detection in a wide range of frequencies. The low power consumption and the modest spectral requirements enabled use of an ordinary audio amplifier to drive the device. In this embodiment, the accelerometer detected the radial components of the acceleration, and the actuator created accelerations parallel to the longitudinal axis of the tool. The device thereby remained stable, even with high feedback gains.

In another embodiment the invention provides a device which allows for the nature of a surface to be assessed, and the tactile information recorded and played back. This may be useful, for example, in teaching, wherein a surgeon's findings during surgery are recorded and played back to students. Due to its spectral characteristics, the amplified tactile signal may be recorded, played back, and/or monitored with an ordinary audio system.

In another embodiment the invention provides feedback to the user using different feedback modes. For example, a component of the acceleration of the tip which is parallel to the longitudinal axis of the tool may be presented to the user by a visual or auditory feedback. Providing this component of the acceleration in a non-tactile format improves the stability of the tool. Components of the acceleration received from the tip by the sensor which are substantially orthogonal to the longitudinal axis of the tool may also be separated and processed so that, for example, one component of the acceleration is provided to the user by tactile feedback while another component is provided by auditory or visual feedback.

Figure 3:
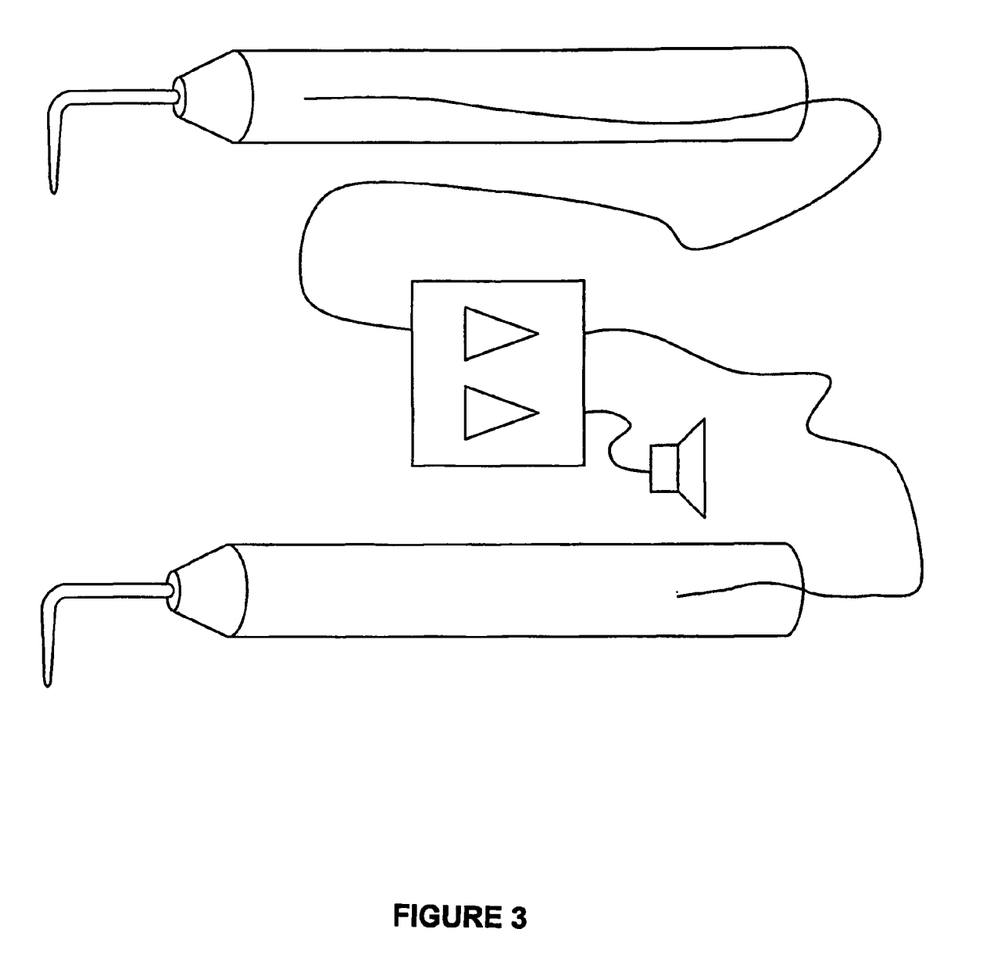
FIG. 3 is a schematic drawing of a system wherein a primary tool provides tactile feedback to a secondary tool.

According to a second aspect of the invention there is provided a system for remote monitoring of the tactile feedback provided by a tool of the invention. An example of such a system is depicted schematically in FIG. 3, and comprises a primary tool for exploring a material of interest. The signal from the primary tool is sent to a processing unit, and the return signal is sent to one or more secondary tools which are not in contact with the material of interest. The primary tool may or may not receive the return signal and produce tactile feedback, depending on the application. Further, the secondary tool(s) may or may not be equipped with a tip and a sensor for receiving information from the tip. Since the actuator is driven by a signal which is independent on (and not aligned with an axis of) the sensed signal, the secondary tool provides a second user (or the second hand of the user of the primary tool) with the tactile feedback information from the material contacted by the primary tool. Such a situation may be useful in teaching, in obtaining a second opinion regarding the nature of a procedure or a tissue under investigation, such as a tumor, or the extent of tissue damage in an area. There may be situations where the user of the primary tool uses one hand to manipulate the tool and the other to experience the surface. Alternatively, an assistant may use the primary tool to investigate a material while another person experiences the amplified tactile and optionally auditory and/or visual feedback remotely. Further, the secondary tool may be used remotely since the signal could be transmitted, for example, over wires, wirelessly, via the telephone, or internet. The detection of a surface or subsurface structure using a remote tool of the invention may be done at the same time as the contact of the primary tool with the surface or subsurface, or the detection using the remote tool could be done later since either the sensor signal or the amplified signal could be recorded and played back. In this manner, visual, tactile and audio feedback can be used to confer with others.

A remote tactile detection system as described herein has numerous applications, such as in teaching or obtaining second opinions, as noted above. Further, such a system may be used to provide information to a group such as an audience, where the group would benefit from experiencing tactile, and possibly additionally audio and visual feedback of the signal. In robotics, the primary tool may used on a remotely controlled robot, and the secondary tool used to provide tactile information to the user controlling the robot.

The invention is further described by way of the following non-limiting example.

Example

A prototype of the tool of the invention was built and tested as described below. This tool had a biocompatible metal hook fixedly attached to a cap made of Delrin plastic. The cap was securely inserted into a hollow handle. The handle was made from carbon fiber tubing and was 15 mm in diameter and 180 mm in length. A 2 g dual-axis accelerometer (ADXL311, available from Analog Devices (Norwood, Mass., U.S.A.)) of dimensions 5 mm×5 mm×2 mm was securely placed inside the hollow handle such that it was in constant contact with the cap in which the tool metal tip was embedded. An actuator was created by inserting a magnet (NdFeB) into the hollow handle and attaching the magnet by screws at either end to two pieces of rubber membrane that were attached by glue to the interior walls of the handle. In this way, the magnet was suspended in the middle of the handle and was not in direct contact with the interior walls of the handle.

Two sets of wire coils were wrapped around the circumference of the handle on the exterior of the handle at positions which were in line with the ends of the magnet. Wires connected the accelerometer to a power source and to a processing unit. The processing unit was in turn wired to both of the coils. The processing unit amplified and filtered the signal. Accelerations were sampled with 16-bit resolution at a rate of 48 kHz by a coder-decoder designed for audio signals. The signal was first anti-aliased by digital filters. The anti-aliasing filter was a low-pass finite impulse response filter of order 64, with a 3 dB cut-off frequency at approximately 500 Hz and a stopband attenuation of approximately 50 dB. The stopband was needed to filter out high frequency components that contributed little to tactile sensation, while keeping the passband as flat as possible. After anti-aliasing, the signal was down-sampled to 2,400 Hz. By limiting the bandwidth of the output, down-sampling increased the stability of the system and eased the design of filters targeting only the frequency range of tactile sensations. The main filter was used for additional processing. Before the output signal was sent to the coder-decoder, its sampling rate was converted back to 48 kHz. This was done with a zero-order hold filter. The enhanced signal was then returned to the coils of the actuator on the tool and the signal caused disturbances in the magnet which caused it to move in the direction of the longitudinal axis of the tool. These movements did not disturb the tool tip at the surface, but they were detectable by the tool handler.

Figure 4:
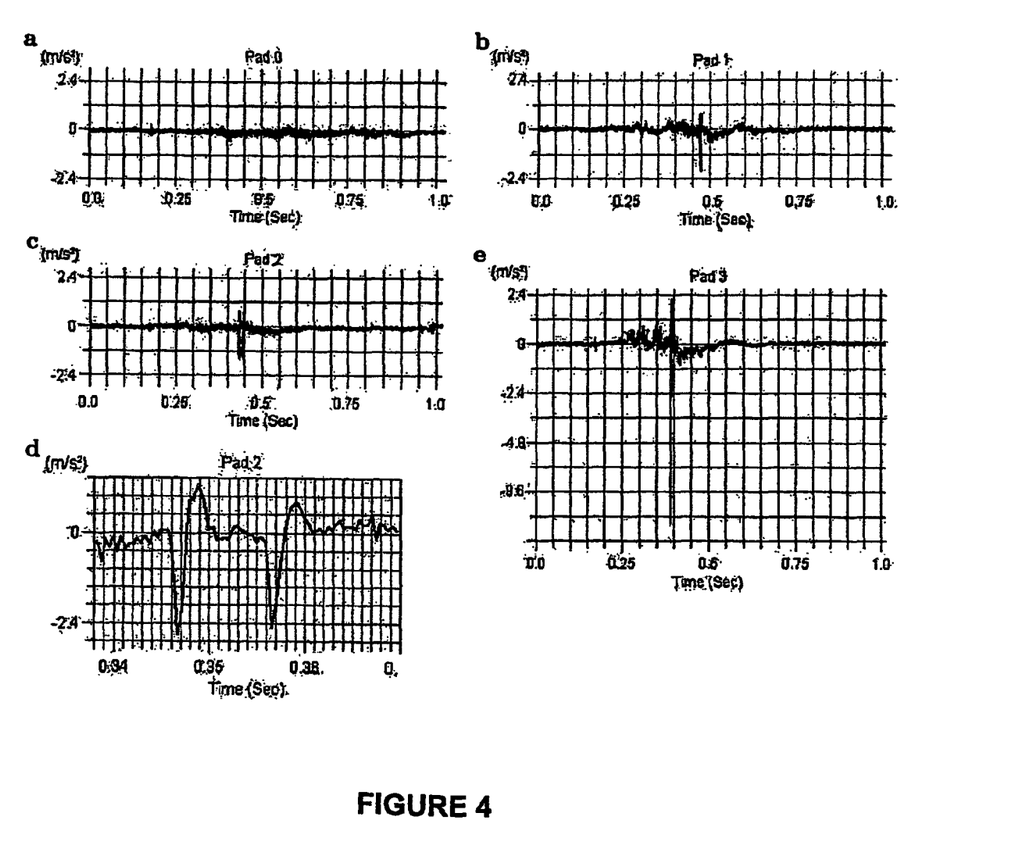
FIG. 4 shows five graphs of acceleration ($m/s^2$) over time (sec) depicting the detection of structures on Viton® surfaces by the tool described in Example 1. In (a) the surface had no cut and the amplitude was modulated by varying the pressure of the tool on the surface; in (b) the graph shows a single signal peak indicating detection of a shallow surface cut; in (c) the graph shows a double signal peak indicating detection of two shallow surface cuts; in (d) the graph is an enlarged view of (c); and in (e) the graph shows a single peak of an magnitude that indicates a deep cut has been detected.

A preliminary test to demonstrate the utility of the prototype tool was conducted by detecting a tear in the surface of a cartilage-like artificial material under different conditions. FIG. 4 shows five graphs of acceleration (m/s$^2$) over time (sec) depicting the detection of structures on Viton® surfaces. In (a) the surface had no cut and the amplitude was modulated by varying the pressure of the tool on the surface; in (b) the graph shows a single signal peak indicating detection of a shallow surface cut; in (c) the graph shows a double signal peak indicating detection of two shallow surface cuts; in (d) the graph is an enlarged view of (c); and in (e) the graph shows a single peak of an magnitude that indicates a deep cut has been detected.

To further demonstrate the utility of the prototype tool, it was tested during the task of detecting a tear in the surface of a cartilage-like artificial material under different conditions. Eight individuals were recruited as subjects for the trials. During the trials, two identical tools of the invention were connected to the signal processing system. Subjects sat at a table and held one of the tools in his/her dominant hand (this then became known as the primary tool). Users then used the primary tool to explore the surface of the Viton® samples while trying to maintain a constant exploration speed. The other tool (known as the secondary tool) was held in the user's non-dominant hand during the trails known as PASSIVE, described below.

In all of the trials, the subjects were asked to gently drag the tool across the surface of four 10 mm×30 mm×3 mm Viton® pads which were glue-mounted on small boxes for easy handling. Viton® is a high performance fluoroelastomer that resembles cartilage. Prior to the trials, cuts were made on the surface of the Viton® pads with a sharp blade which protruded by a set distance out of a block of rubber. One pad had no cut, another had a 1.5 mm-deep-cut, another had two 1.5 mm-deep-cuts, and the fourth had a cut 3 mm-deep (the material was cut through). The lighting condition in the room during all of the trials was semi darkness so that the users could not visually assess the surfaces while still being able to handle the blocks.

During the trials if the tool contacted a crack in the surface while being dragged across the surface, the tool tip dipped slightly into the crack. This dipping motion was detected by the accelerometer sensor and was amplified by the processing unit and the amplified signal was sent to the actuator which induced a transient vibratory motion in the tool. This signal could be readily detected by the tool handler. If the crack was sufficiently deep relative to the radius of the tool tip, the tip would catch the lip of the crack and produce a large transient tactile signal.

During each trial, a sequence of 24 pads was given to each subject in a randomized order, each pad being presented 6 times. Subjects were asked to detect if there was a cut in the pad. They had to decide rapidly and answered by pressing keys labeled yes and no. Trials were done under the following four conditions in the following order and the duration of each testing session was less than one hour.

During the first trial which is known as HAPTIC, only one of the tools was handled by the user. The tool provided an amplified tactile feedback to the tool itself which was readily detectable to the handler.

During the second trial which is known as AUDIO, again only one of the tools was handled by the user. In this trial, the only feedback provided to the user was an audio signal derived from the signal created in the tool accelerometer upon contacting the tool with a surface anomaly and the signal being sent to the processing unit and on to an loudspeaker.

During the third trial which is known as PASSIVE, subjects held both of the tools. The primary tool was held in the user dominant hand while the secondary tool was passively held in the user's non-dominant hand. The primary tool was used to contact the surface at approximately a consistent speed, but it did not provide any amplified tactile feedback to the user. Instead, the amplified tactile feedback was sent to the secondary tool only.

In the fourth trial which is known as OFF, subjects used the tool without any amplified tactile or audio feedback.

The results of the four trials are summarized in the Table 1 below. Table 1 shows that the performance of the subjects improved with haptic and sound feedback over no amplified feedback. These results support previous findings that haptic and audio cues both contribute to the perception of surface roughness (Lederman, et al 2002). Audio feedback improved the performance by approximately 20%, and haptic feedback by 10%. One-way analysis of variance (anova) of the three conditions OFF, HAPTIC and AUDIO confirmed the significance of the differences ($p=0.015$, $p<0.05$). The anova test applied to pairs of conditions yielded $p=0.015$ between the AUDIO and OFF, and $p=0.055$ between HAPTIC and OFF conditions. There was no significant difference between HAPTIC and PASSIVE conditions ($p=0.15$, $p>0.05$). Deep cuts were almost perfectly detected. For pads with small cuts, the performance in HAPTIC, AUDIO, and PASSIVE was better than in the OFF condition. When there was no amplified feedback, the subjects failed to detect the presence of small cuts most of the time.

TABLE 1

Summary of Percentages of Correct Answers for the four assessment conditions for the 4 different Viton ® blocks.

| Condition | No cut | 1 shallow cut | 2 shallow cuts | 1 deep cut |
| --- | --- | --- | --- | --- |
| OFF | 92 | 15 | 33 | 100 |
| HAPTIC | 90 | 44 | 65 | 100 |
| AUDIO | 90 | 63 | 77 | 100 |
| PASSIVE | 50 | 60 | 65 | 98 |

Thus the system was able to improve the performance of subjects in detecting superficial cuts in a cartilage-like material. Performance with audio feedback was consistently better than with haptic feedback, which may be due to the fact that the auditory system used allowed subjects to detect small transients out of a noisy background better than the tactile feedback system. The inventors expect that when using the two combined modalities of touch and audio cues, sensitivity may increase further. Another possible explanation of the improved performance with audio feedback is that some information may have been lost in the actuator signal filtering process. During the trails, the signals to the loudspeakers were not processed, but the signals to the actuators for haptic feedback were filtered and downsampled in an attempt to eliminate sensor noise. Even though the 400 Hz threshold was imposed during the filtering, there may be some useful information above this frequency. Signal enhancement techniques beyond plain amplification in a frequency band may be useful.

Our preliminary study found that significant task improvement happened when either haptic or auditory feedback were presented. The device also made it possible to experience a surface remotely. The device can be used as a texture-recording/play instrument, with considerable potential for use in surgical simulation and training.

All publications listed and cited herein are incorporated by reference in their entirety.

It will be understood by those skilled in the art that this description is made with reference to the preferred embodiments and that it is possible to make other embodiments employing the principles of the invention which fall within its spirit and scope as defined by the claims

REFERENCES

1. Dario, P., Hannaford, B., and Menciassi, A. "Smart Surgical Tools and Augmenting Devices", *IEEE T on Robotics and Automation*, 19(5):782-792 (2003).
2. Kontarinis, D. A., and Howe, R. D. "Tactile Display of Vibratory Information in Teleoperation and Virtual Environments", *Presence*, 4(4):387-402 (1995).
3. Lederman, S. J., Klatzky, R. L., Hamilton, C., Morgan, T. "Integrating multimodal information about surface texture via a probe: Relative contributions of haptic and touch produced sound sources", Proc. Symp. On Haptic Interfaces for Virtual Environment and Teleoperator Systems, 97-104 (2002).
4. Okamura, A. M., Cutkosky, M. R., and Dennerlein, J. T. "Reality-Based Models for Vibration Feedback in Virtual Environments", *IEEE/ASME T. on Mechatronics*, 6(3):245-252 (2001).
5. Pai, K. and Rizun, P. R. "The WHaT: "A Wireless Haptic Texture Sensor". Proc. *Eleventh Symposium on Haptic Interfaces for Virtual Environment and Teleoperator Systems* (2003).
6. Rosen, J., Hannaford, B., MacFarlane, M. P., and Sinanan, M. N. "Force controlled and teleoperated endoscopic grasper for minimally invasive surgery experimental performance evaluation", *IEEE T on Biomedical Engineering*, 46(10):1212-1221 (1999).
7. Yao, H.-Y., et al. "A tactile enhancement instrument for minimally invasive surgery". *Computer Aided Surgery* (2005) (in press).
8. Yao, H.-Y. "Touch magnifying instrument applied to minimum invasive surgery". M. Eng. Thesis, McGill University, September 2004.

We claim:

1. A tool for obtaining tactile information about a material, comprising:
a tip for interacting with the material to produce a vibration;
a handle attached to the tip;
a sensor in mechanical communication with the tip, the sensor receiving vibration from the tip and producing an electrical signal from the vibration;
an amplifier for receiving and amplifying the electrical signal to produce an amplified signal; and
an actuator disposed in the handle for receiving the amplified signal and producing related output motion;
wherein the output motion of the handle is in a direction different from that of the vibration at the tool tip.

2. The tool of claim 1, wherein the vibration of the tip is along a first axis and the output motion is along a second axis different from the first axis.

3. The tool of claim 2, wherein the vibration of the tip is along a first axis and a second axis different from the first axis, and the output motion is along a third axis different from the first axis and the second axis.

4. The tool of claim 1, further comprising an audio transducer for receiving the amplified signal and producing an audio output.

5. The tool of claim 1, wherein the output motion is along an axis parallel to a longitudinal axis of the tool.

6. The tool of claim 1, wherein the sensor is an accelerometer.

7. The tool of claim 2, wherein the first and second axes are orthogonal.

8. The tool of claim 3, wherein the first, second, and third axes are orthogonal.

9. The tool of claim 1, wherein the output motion is a vibration.

10. The tool of claim 1, wherein the actuator comprises:
a magnet resiliently suspended inside the handle; and
a wire coil proximal to the magnet, the coil receiving the amplified signal;
wherein the amplified signal induces motion of the magnet relative to the coil and the handle.

11. The tool of claim 1, wherein the tool is a surgical instrument.

12. A system for remotely obtaining tactile information about a material, comprising:
a primary tool according to claim 1; and
at least one secondary tool, each secondary tool comprising:
a handle; and
an actuator disposed in the handle for receiving the amplified signal from the primary tool and producing an output motion in the handle.

13. The system of claim 12, wherein the vibration of the tip is along a first axis and the output motion is along a second axis different from the first axis.

14. The system of claim 12, wherein the vibration of the tip is along a first axis and a second axis different from the first axis, and the output motion is along a third axis different from the first axis and the second axis.

15. The system of claim 12, wherein the sensor is an accelerometer.

16. The system of 12, wherein the tool is a surgical instrument.

17. A method for obtaining tactile information about a material, comprising:
providing a tool having a handle and a tip for interacting with the material to produce a vibration;
contacting the material with the tip;
sensing vibration of the tip and converting the vibration into an electrical signal;

amplifying the signal to produce an amplified signal; and
producing output motion in the handle using the amplified signal, the output motion related to the vibration of the tip;
wherein the output motion of the handle is in a direction different from that of the vibration at the tool tip.

18. A method for remotely obtaining tactile information about a material, comprising:
providing a primary tool according to the method of claim 17;
providing at least one secondary tool, each secondary tool comprising:
a handle; and
an actuator disposed in the handle for receiving the amplified signal and producing an output motion in the handle; and
producing output motion in each secondary tool using the amplified signal from the primary tool.

19. The method of claim 17, wherein sensing vibration comprises sensing vibration along a first axis, and producing output motion comprises producing motion along a second axis different from the first axis.

20. The method of claim 17, wherein the method relates to a surgical procedure.

21. The method of claim 17, wherein sensing vibration comprises sensing vibration along a first axis and a second axis different from the first axis, and producing output motion comprises producing motion along a third axis different from the first axis and the second axis.

22. The method of claim 17, comprising producing the output motion along an axis parallel to a longitudinal axis of the tool.

23. The method of claim 17, wherein the first and second axes are orthogonal.

24. The method of claim 21, wherein the first, second, and third axes are orthogonal.

* * * * *